Figure 1:
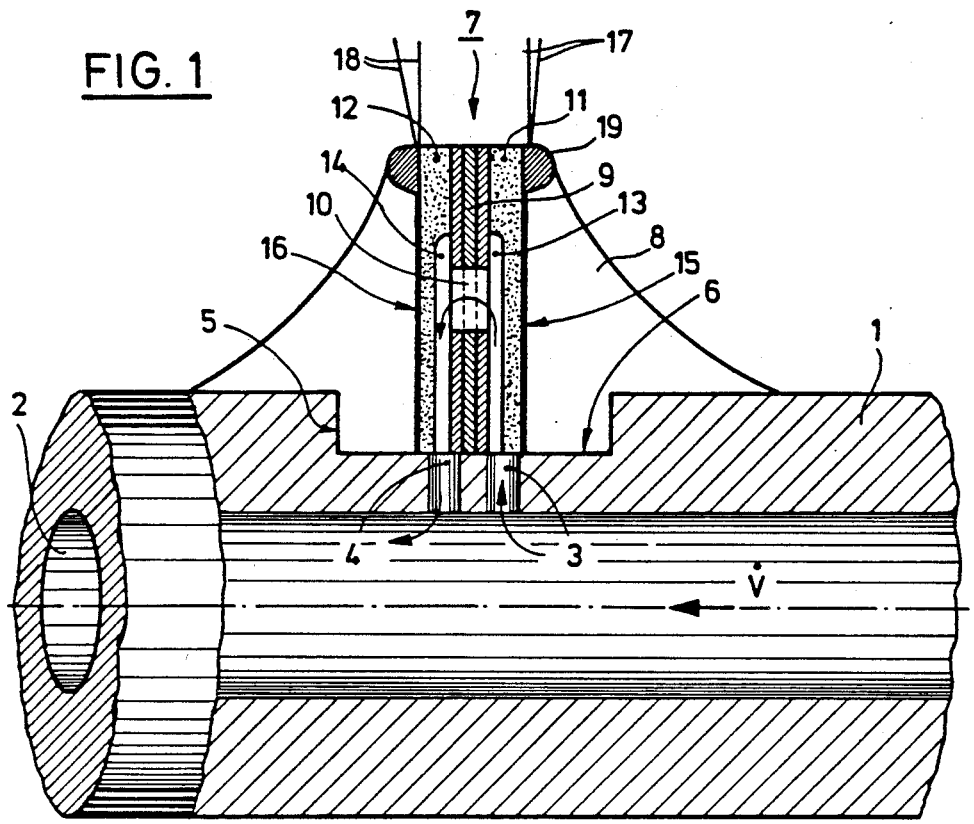

United States Patent [19]

Wiegleb

[11] Patent Number: 4,850,714
[45] Date of Patent: Jul. 25, 1989

[54] APPARATUS FOR MEASURING THE THERMAL CONDUCTIVITY OF GASES

[75] Inventor: Gerhard Wiegleb, Maintal, Fed. Rep. of Germany

[73] Assignee: Leybold Aktiengesellschaft, Hanau, Fed. Rep. of Germany

[21] Appl. No.: 178,820

[22] Filed: Mar. 29, 1988

Related U.S. Application Data

[63] Continuation of Ser. No. 822,768, Jan. 24, 1986, abandoned.

[30] Foreign Application Priority Data

Jan. 25, 1985 [DE] Fed. Rep. of Germany ....... 3502440

[51] Int. Cl.$^4$ ............................................ G01N 27/18
[52] U.S. Cl. ..................................... 374/44; 73/27 R
[58] Field of Search ............ 73/27 R, 204; 338/22 R, 338/22.5 D, 34, 58, 254, 255, 283, 290, 293, 315, 318; 374/10–13, 29–41, 43, 44, 135, 166, 183, 188; 323/365, 366, 369

[56] References Cited

U.S. PATENT DOCUMENTS

| 2,329,840 | 9/1943 | Keinath | 73/27 R |
| 3,606,790 | 9/1971 | Matsumoto et al. | 73/27 R |
| 3,768,301 | 10/1973 | Feichtinger | 73/27 R |
| 3,888,110 | 6/1975 | Clark | 73/27 R |
| 4,074,566 | 2/1978 | Obayashi et al. | 73/204 |
| 4,395,907 | 8/1983 | Morita et al. | 73/202 |
| 4,461,166 | 7/1984 | Gatten et al. | 73/27 R |

FOREIGN PATENT DOCUMENTS

| 1256909 | 12/1967 | Fed. Rep. of Germany . |
| 1803208 | 6/1969 | Fed. Rep. of Germany . |
| 2209413 | 9/1973 | Fed. Rep. of Germany . |
| 2229464 | 6/1974 | Fed. Rep. of Germany . |
| 2311103 | 9/1974 | Fed. Rep. of Germany ..... 73/27 R |
| 2156752 | 11/1975 | Fed. Rep. of Germany ..... 73/27 R |
| 2952137 | 5/1981 | Fed. Rep. of Germany ........ 374/44 |
| 3047601 | 7/1982 | Fed. Rep. of Germany . |
| 104720 | 8/1980 | Japan ..................................... 73/204 |
| 830224 | 5/1981 | U.S.S.R. ................................ 374/44 |

OTHER PUBLICATIONS

Elektrowärme Theorie und Praxis, pp. 163 and 164.

Primary Examiner—William A. Cuchlinski, Jr.
Assistant Examiner—W. Morris Worth
Attorney, Agent, or Firm—Felfe & Lynch

[57] ABSTRACT

Apparatus for measuring the thermal conductivity of a gas has first and second, heatable and temperature-dependent measuring resistors in sufficiently close, tandem proximity along a flow path for the gas and connected in opposite arms of a measuring bridge circuit.

6 Claims, 2 Drawing Sheets

U.S. Patent Jul. 25, 1989 Sheet 2 of 2 4,850,714

APPARATUS FOR MEASURING THE THERMAL CONDUCTIVITY OF GASES

This application is a continuation of application Ser. No. 822,768, filed Jan. 24, 1986, now abandoned.

The invention relates to an arrangement for measuring the thermal conductivity of gas.

Arrangements of this type are usually used in gas analyzing devices as individual gases differ from each other in having different coefficients of thermal conductivity. The main disadvantage of such arrangements and measuring resistors is that the measured values are to a great extent dependent on the flow rate of the medium under analysis. Thus, for example, a higher rate of flow simulates a greater thermal conductivity, i.e. the stability of the output signal is dependent on varying flows. In principle this can be expressed as follows: the detector is not in a position to differentiate between cooling by flow and cooling by thermal conduction.

It is, however, impossible to do without a flow, as the composition of the gas may alter and a corresponding speed of response is necessary.

Two requirements stand therefore in diametric opposition to each other, these being on the one hand the need for a high accuracy of measurement and on the other the need for a high speed of response.

An arrangement of the above-described type is known from DE-AS No. 21 56 752, FIG. 6. Here the influence of the flow rate is reduced by the temperature sensor being arranged in a bypass, so that it is only exposed to a partial flow. The lower the flow rate in the bypass the more precise the measured value, but also the longer the response time, and vice versa.

If, at the limit, a gas exchange due to flow is dispensed with completely the accuracy of measurement is correspondingly high, the response time being, however, exceptionally long. A detector of this type, also called a "diffusion cell" because of the principle of gas exchange, is known from DE-PS No. 29 52 137. Here even convection caused by temperature differences is suppressed by the particularly small volume of the measuring cell. The measuring itself is achieved by energy transport as a result of thermal conduction between a heating wire and a temperature measuring wire. In spite of the substantial miniaturization of this method, which is not of the above type, it still suffers from the disadvantage of considerable sluggishness.

The problem on which the invention is based is, therefore, to provide an arrangement of the above-described type which exhibits only very slight flow sensitivity despite a high speed of response.

For the above-described arrangement the solution to this problem is achieved according to the invention (a) by locating a second heatable and temperature-dependent measuring resistor in close proximity to the first measuring resistor, one behind the other along the flow path, and (b) by locating these two measuring resistors electrically in opposite arms of the measuring bridge.

The combination of these two measures brings about a compensation of the flow dependency still present at the individual measuring resistors. When the flowrate is nil a temperature profile forms in the immediate vicinity of the two heated measuring resistors, this temperature profile also being symmetrical with respect to a plane of symmetry between the two measuring resistors. Ideally, therefore, the resistance values of the two measuring resistors are equal. As soon as a flow commences the maximum temperature moves in the direction of the measuring resistor located downstream because of the additional heat transport. The difference occurring in the resistance values due to this temperature difference is a measure of both the flow rate and of the thermal conductivity of the gas or gas mixture concerned. As the two measuring resistors are, according to the invention, arranged electrically in opposite arms of the measuring bridge, the flow rate has opposing and therefore compensatory influences on the two measuring resistors, while the influence of the thermal conductivity is maintained, it being in the same direction in the two measuring resistors.

It goes without saying that even with the method according to the invention miniaturization of the actual measuring cell is advantageous as regards its volume and flow paths, but this is not quite as essential as with the detector according to DE-PS No. 29 52 137.

Let us take, for example, the ratio of bypass flow to total flow as being 1:1000. With a cell volume of around 5 mm$^3$ a time constant of around 0.3 seconds is then obtained, caused by purging. By means of appropriately constructed measuring resistors with a material thickness of, for example, 5 μm, a time constant of under 0.1 seconds can be achieved for the detector, such that response times of less than 0.4 seconds can be obtained. With the help of the detailed description it will be shown that these values can be even further reduced.

Although it is already known from DE-Gbm No. 1 920 597 and DE-AS No. 1 256 909 to connect heated measuring resistors behind each other in the direction of flow and to detect changes in resistance by means of a measuring bridge, this measure is taken for the opposite purpose, that is to say for detecting mass flows. Here the heated, temperaturedependent measuring resistors are arranged in the same bridge arm, so that the effect of heat transfer by flow behaves additively.

According to another modification of the invention it is particularly advantageous for the two measuring resistors to be of serpentine construction and arranged in a through window in a supporting body, which may be constructed in a layered manner from three insulating, congruent lamellae.

It is also advantageous for the supporting body to be arranged between ceramic plates, each of which is provided with its own heating resistor by means of which the measuring cell can be heated controllably to a constant temperature.

As the thermal conduction in the direction of the cell wall is proportional to the difference in temperature between the measuring resistor on the one hand and the cell wall on the other, the thermostatically controlled heating of the measuring cell ensures additional accuracy of measurement.

Further advantageous developments of the subject of the invention arise from the remaining subordinate claims.

Figure 5:
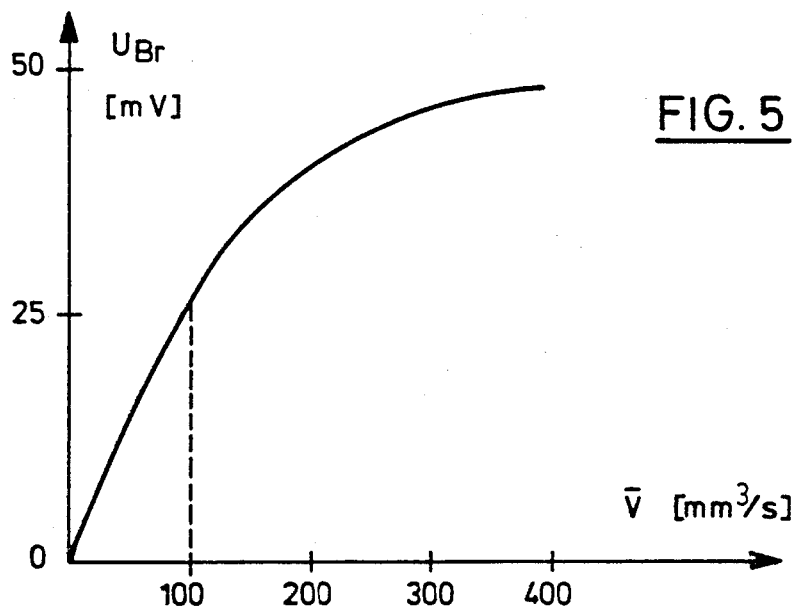
Figure 2:
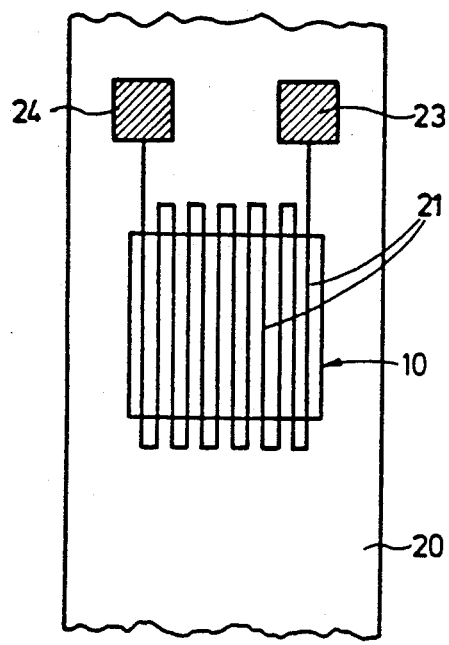
Figure 3:
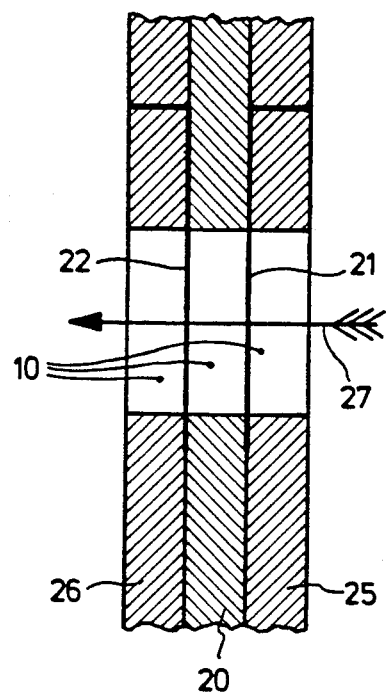
Figure 4:
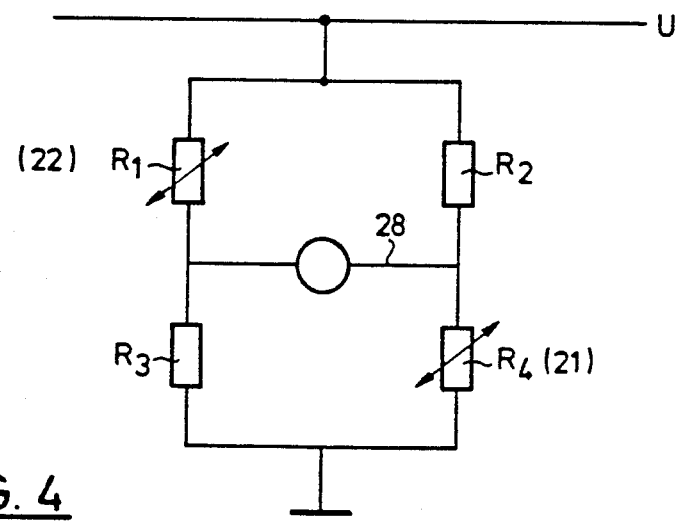

One embodiment of the subject of the invention and its method of operation are described in more detail below, with reference to FIGS. 1 to 5 in which:

FIG. 1 is a longitudinal sectional view of the flow channels in a measuring cell, which is positioned radially on a main flow channel, FIG. 2 is a plan view of the central insulating lamella of the layered supporting body, FIG. 3 shows an enlarged portion of FIG. 1, namely the supporting body including the central lamella of FIG. 2, FIG. 4 shows the electric arrangement of the measuring resistors inside a measuring bridge and FIG. 5 shows the characteristic curve for the flow dependency of each of the two measuring resistors.

In FIG. 1 there is shown a main flow channel 1 with a longitudinal bore 2 which, for example, has a diameter of 3 mm. The main flow channel has two radial branch bores 3 and 4 in close proximity to each other, these each having a diameter of 0.5 mm. In the region of these branch bores the main flow channel 1 is provided with a recess 5 with a flat base area 6.

On the base area 6 there is positioned the measuring cell 7 itself, which is described in more detail below. It is firmly connected to the main flow channel 1 by means of a pourable sealing compound 8 which may, for example, be a silicone resin.

The central section of the measuring cell 7 is a supporting body 9 with a window 10, the details of which are explained more closely with reference to FIG. 3. The supporting body 9 is arranged between two ceramic plates 11 and 12, one of which comprises a flow channel 13 leading towards the window 10 and the other of which comprises a flow channel 14 leading away from the window 10. The two flow channels 13 and 14 communicate with the radial branch bores 3 and 4, so that the flow indicated by arrows can develop through the window 10.

The ceramic plates 11 and 12 each have a heating resistor 15 and 16 on their outer sides, which heating resistors 15 and 16 are constructed as platinum thin-film resistors. The two heating resistors act simultaneously as measuring resistors for the thermally regulated temperature control of the cell 7. This combination of heating and regulation provides excellent control accuracy with very good constancy of temperature. The heating resistors 15 and 16 are supplied with power via connecting wires 17 and 18. In addition, the measuring cell 7 is equipped with a pull relief 19 consisting of glass and also embedded in the sealing compound 8. The ceramic plates 11 and 12 are 0.6 mm thick, whence the smallness of the whole arrangement arises.

FIG. 2 shows the central insulating lamella 20 of the supporting body 9 with the approximately square window 10. On each side of the lamella 20 there is located a serpentine measuring resistor 21 and 22, each one spanning the window several times (only the measuring resistor 21 is visible in FIG. 2). The ends of each of the measuring resistors lead to connecting contacts 23 and 24. The measuring resistors may be manufactured, for example, by masking and chemically etching a small nickel sheet 5 μm thick.

FIG. 3 shows the central lamella 20 embedded between two more insulating lamellae 25 and 26 with congruently positioned windows 10 of the same size. The arrangement is such that the first measuring resistor 21 lies between the first lamella 25 and the second (central) lamella 20, and the second measuring resistor 22 lies between the second lamella 20 and the third lamella 26, the measuring resistors spanning the congruent windows in the manner shown in FIG. 2. As indicated, the individual windows 10 form the flow path 27, symbolized by the arrow marked, and in this flow path there lie one behind the other the two measuring resistors 21 and 22.

FIG. 4 shows the measuring bridge with the bridge resistors $R_1$, $R_2$, $R_3$ and $R_4$ located in the individual bridge arms. The bridge resistors $R_1$ and $R_4$ form the measuring resistors 22 and 21 respectively, and the voltage tapped off from the bridge diagonal is a measure of the thermal conductivity of the gas present in the flow path 27.

Compensation of the flow influence is effected by the flow-occasioned heat transfer from measuring resistor 21 to measuring resistor 22. Owing to the measuring resistors 21 and 22 being arranged opposingly in the measuring bridge, the effect of thermal conduction behaves additively, while the effect of heat transfer due to flow behaves subtractively, because the thermal energy conducted away from measuring resistor 21 is fed to measuring resistor 22. Within set limits of the characteristic curve shown in FIG. 5 compensation of flow dependency is therefore achieved. According to FIG. 5 the linear compensation range of the two measuring resistors used reaches around 100 mm$^3$/ sec., compensation of the flow rate therefore being ensured when the total throughput through the main flow channel 1 is 1 l/min (1 liter per minute) and the bypass fraction is 1/1000. The bypass is formed, in accordance with FIG. 1, by the branch bore 3, the radial flow channel 13, the window arrangement 10, the second radial flow channel 14 and the branch bore 4.

In an embodiment according to FIG. 1 the chamber volume of the measuring cell 7, i.e. the volume of the flow channels 13 and 14 and of the window arrangement 10, amounted to around 1 mm$^3$. The two measuring resistors 21 and 22 spanned a window area of 1 mm×1 mm and had a resistance of 22.5 ohms. In this embodiment, with practically imperceptible flow dependency or completely satisfactory flow compensation the speed of response, or $T_{90}$-time, was 800 milliseconds, that is the time required for the measured value to reach 90% of the theoretical value.

The measuring resistors 21, 22 are heatable, that is, they produce heat in use, in this case from the current of the bridge circuit in which they are connected, for example. Gas flow along the flow path from resistor 21 to resistor 22 thus carries some of the heat produced in resistor 21 from resistor 21 to resistor 22 which replaces some of the heat and, ideally, a like amount, similarly carried from resistor 22 by the flow.

This defines the sufficiently close proximity of the measuring resistors 21, 22. That is, the measuring resistors 21, 22 must be in proximity sufficiently close for the gas flow to carry at least some and, preferably, most or, even, substantially all of the heat carried from measuring resistor 21 to measuring resistor 22 relative to heat losses therebetween.

The gas flow thus affects the temperature and, thus, the dependent resistance of resistor 21 more than resistor 22 and at least generally proportionally to the flow. The amount of the temperature and, thus, the resistance of each resistor 21, 22 are affected by the flow also depends, however, on the thermal conductivity of the gas and, because the gas at each resistor is the same, this effect is substantially the same for both resistors. Then, because the measuring resistors 21, 22 are respectively in opposite arms of the bridge, meaning diagonally opposite arms as shown in FIG. 4, the effect of the flow on the resistors 21, 22 is subtractive. On the other hand, the effect of the thermal conductivity is additive on the balance of the bridge (in line 28 of FIG. 4), i.e. the bridge compensates for the flow effect and the thermal conductivity is indicated by the magnitude of bridge unbalance. Since the resistors are in close proximity, any change in voltage across the bridge is due to thermal conductivity of the gas, the influence of flow speed having been compensated for.

It will be understood that the specification and examples are illustrative but not limitative of the present invention and that other embodiments within the spirit and scope of the invention will suggest themselves to those skilled in the art.

What is claimed is:

1. Apparatus for measuring thermal conductivity of a gas, comprising:

means defining a main flow path for the gas; by-pass means defining a second gas flow path, at least a portion of which extends radially of the main flow path;

first and second, heatable and temperature-dependent measuring resistors in sufficiently close proximity to each other one behind the other, in tandem, along the by-pass flow path;

a measuring bridge circuit for measuring the thermal conductivity of said gas having arms and the first and second measuring resistors respectively in opposite ones of the arms of the measuring bridge;

said by-pass means comprising a supporting body of three, congruently-windowed, insulating lamellae with the first and second lamellae and the second and third lamellae respectively supporting the first and second measuring resistors therebetween, said first and second measuring resistors spanning the congruent windows thereof, the supporting body additionally comprising at least one ceramic plate along the three lamellae for defining therebetween portions of the second flow path of the by-pass means which extend from opposite sides of the congruent windows of the lamellae and said radially extending portion;

said at least one ceramic plate having at least one resistor means on a side of the ceramic plate opposite the lamellae for heating the ceramic plate controllably to a constant temperature.

2. The apparatus of claim 1, wherein each measuring resistor has a serpentine construction across the flow path of the by-pass means.

3. The apparatus of claim 1, wherein the total volume of the flow path of the by-pass means is less than 5 mm$^3$.

4. The apparatus of claim 2, wherein the total volume of the flow path of the by-pass means is less than 5 mm$^3$.

5. The apparatus of claim 1, wherein the total volume of the flow path of the by-pass means is less than 1 mm$^3$.

6. The apparatus of claim 2, wherein the total volume of the flow path of the by-pass means is less than 1 mm$^3$.

* * * * *